(12) United States Patent  
Park et al.

(10) Patent No.: US 8,101,114 B2  
(45) Date of Patent: Jan. 24, 2012

(54) PARTICLE BASED MOLDING

(75) Inventors: Jung-hwan Park, Atlanta, GA (US);  
Mark G. Allen, Atlanta, GA (US);  
Mark R. Prausnitz, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 370 days.

(21) Appl. No.: 12/299,092

(22) PCT Filed: Apr. 30, 2007

(86) PCT No.: PCT/US2007/067776  
§ 371 (c)(1),  
(2), (4) Date: Apr. 20, 2009

(87) PCT Pub. No.: WO2007/127976  
PCT Pub. Date: Nov. 8, 2007

(65) Prior Publication Data  
US 2010/0048744 A1    Feb. 25, 2010

Related U.S. Application Data

(60) Provisional application No. 60/796,419, filed on May 1, 2006.

(51) Int. Cl.  
*A61K 9/14* (2006.01)

(52) U.S. Cl. ........ 264/443; 264/442; 264/460; 424/489; 424/484; 424/486

(58) Field of Classification Search .................. 264/442, 264/443, 445, 240, 460  
See application file for complete search history.

(56) References Cited

U.S. PATENT DOCUMENTS

| | | | | |
|---|---|---|---|---|
| 4,288,398 | A * | 9/1981 | Lemelson | 264/443 |
| 4,957,668 | A * | 9/1990 | Plackard et al. | 264/427 |
| 2002/0017165 | A1 | 2/2002 | Lebeau et al. | |
| 2002/0082543 | A1 | 6/2002 | Park et al. | |
| 2004/0012124 | A1 * | 1/2004 | Li et al. | 264/460 |
| 2004/0121066 | A1 | 6/2004 | Anderson et al. | |
| 2005/0251088 | A1 | 11/2005 | Kwon | |
| 2008/0088066 | A1 * | 4/2008 | Ferguson et al. | 264/443 |
| 2010/0003158 | A1 * | 1/2010 | Ando et al. | 419/66 |

OTHER PUBLICATIONS

International Search Report and Written Opinion in related, co-pending PCT Application No. PCT/US07/067776, dated Dec. 4, 2007.

* cited by examiner

*Primary Examiner* — Susan W Berman  
(74) *Attorney, Agent, or Firm* — Jihan A. R. Jenkins, Esq.; Ryan A. Schneider, Esq.; Troutman Sanders LLP

(57) ABSTRACT

Various apparatuses, arrangements, and methods are provided for creating various structures including microstructures. In one embodiment, a method for creating a microstructure is provided comprising packing a plurality of particles into a micromold, and then applying energy to the particles in the micromold. As a result of the application of energy, a microstructure is formed in the micromold out of the particles. Thereafter, the microstructure is removed from the micromold.

6 Claims, 9 Drawing Sheets

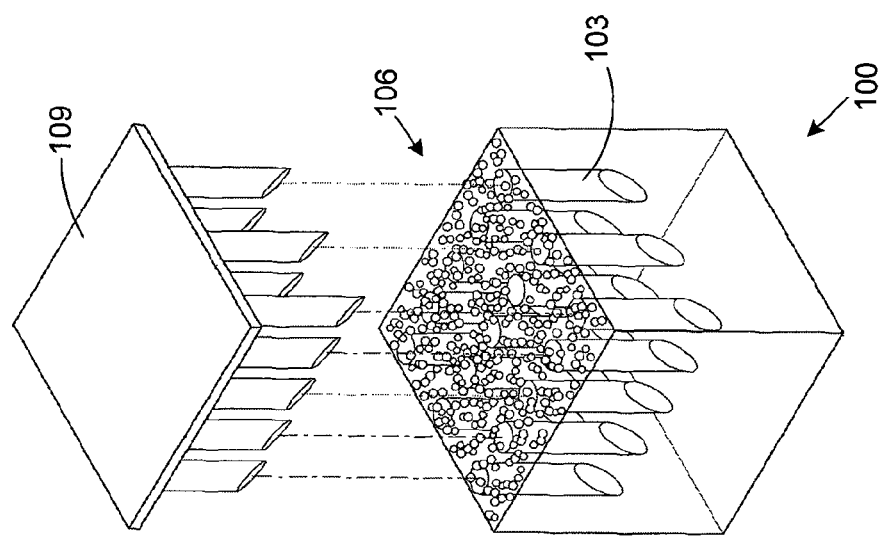
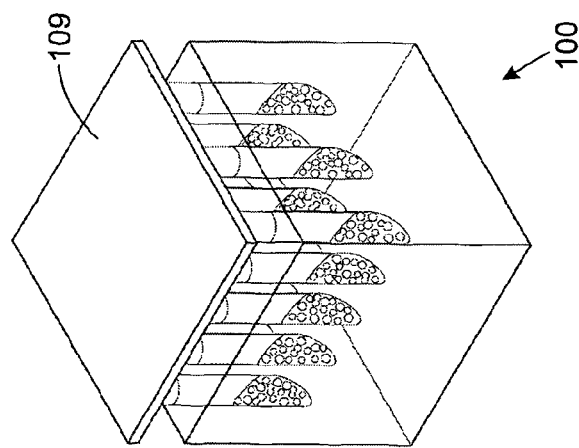

PARTICLE BASED MOLDING

CROSS REFERENCE TO RELATED CASES

This application claims priority to co-pending International Patent Application PCT/US2007/067776 entitled "Particle Based Molding," filed on Apr. 30, 2007, which is incorporated herein by reference in its entirety, and which claims priority to U.S. Provisional Patent Application 60/796,419 entitled "Methods and Devices for Delivery to Skin and Other Applications," filed on May 1, 2006, which is also incorporated herein in its entirety.

STATEMENT REGARDING FEDERALLY SPONSORED RESEARCH OR DEVELOPMENT

This invention was made with government support under contract number 8 R01 EB00260-03, awarded by the National Institutes of Health. The government has certain rights in the invention.

BACKGROUND

Conventional micromolding techniques use injection molding concepts to fill micromolds with melted polymer materials. However, the conventional micromolding techniques are limited in that they only use single-composition substances when creating microstructures. Also, microstructures having high aspect ratios and complex geometries are difficult to create using injection molding techniques because the high viscosity of polymer melt leads to premature cooling before the polymer completely fills the mold cavity. Also, the high temperatures and pressures of traditional processing can be detrimental to molding materials and prohibit the concept of multi-composition and multi-geometric structures.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIGS. 1A through 1F are drawings that illustrate the creation of various structures according to various embodiments of the present invention;

DETAILED DESCRIPTION OF THE PREFERRED EMBODIMENT

Figure 1D:
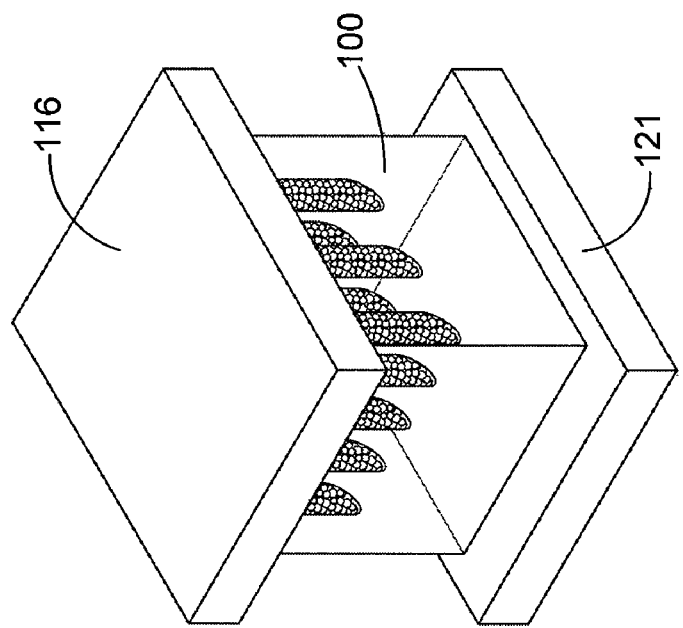

Referring to FIGS. 1A through 1F, shown is a method by which a microstructure is created according to an embodiment of the present invention. As shown, a micromold 100 is provided that includes cavities 103 that are filled with particles 106. Energy is applied to the micromold containing the particles 106, thereby resulting in the creation of the microstructures in the micromold 100. A detailed explanation of the various steps taken to create a microstructure as depicted in FIGS. 1A through 1F is provided below after a description of the structural components depicted.

The micromold 100 may be constructed from various materials such as, for example, polymers including poly-di-methyl-siloxane (PDMS) and poly(methyl methacrylate) (PMMA); metals, whether conventionally machined or electroformed; ceramics, or other appropriate materials. The micromold 100 may be constructed, for example, by using a process in which (i) a female master is created photolithographically out of SU-8 epoxy photoresist, (ii) a male master is molded out of PDMS from the female master mold, and (iii) a female replicate mold is created out of PDMS from the male master structure. For further discussion of the creation of the micromold 100, reference is made to Jung-Hwan Park, et al. "Polymer Particle-Based Micromolding to Fabricate Novel Microstructures," Biomed Microdevices, Vol. 9, pp. 223-234 (2007), which is incorporated herein by reference.

The particles 106 may comprise, for example, biodegradable polymers such as poly-lactic acid (PLA), poly-glycolic acid (PGA), and their copolymers (PLGA). Such materials facilitate the creation of microstructures that may be used for medical applications as they safely degrade into biocompatible monomers in the body and are approved by the Food and Drug Administration. This class of polymer microparticles has been studied extensively to encapsulate compounds such as drugs for sustained release for many applications, including vaccine delivery, cancer treatment, hormone therapy, protein delivery, gene delivery, and diagnostic applications. For further discussion regarding the use of polymer microparticles to encapsulate various compounds set forth above, reference is made to the following published articles, each of these published articles being incorporated herein by reference:

H. J. Lee, G. Riley, O. Johnson, J. L. Cleland, N. Kim, M. Charnis, L. Bailey, E. Duenas, A. Shahzamani, M. Marian, A. J. S. Jones, and S. D. Putney, "In vivo characterization of sustained-release formulations of human growth hormone," J. Pharmacol. Exp. Ther. 281, 1431-1439 (1997a).

H. K. Lee, J. H. Park, and K. C. Kwon, "Double-walled microparticles for single shot vaccine," J. Control. Rel. 44, 283-293 (1997b).

D. T. Birnbaum, and L. Brannon-Peppas, *Microparticle drug delivery systems*. in Cancer Drug Discovery and Development, edited by D. M. Brown (Human Press, Totowa, N.J., 2003) pp.117-135.

D. Jain, A. K. Panda, and D. K. Majumdar, Eudragit, "S100 entrapped insulin microspheres for oral delivery," AAPS PharmSciTech. 6, E100-E107 (2005).

S. R. Little, D. M. Lynn, Q. Ge, D. G. Anderson, S. V. Puram, J. Chen, H. N. Eisen, and R. Langer, "Poly-B amino ester-containing microparticles enhance the activity of nonviral genetic vaccines," Proc. Natl. Acad. Sci. (USA) 101, 9534-9539 (2004).

S. J. Lee, J. R. Jeong, S. C. Shin, J. C. Kim, Y. H. Chang, K. H. Lee, and J. D. Kim, "Magnetic enhancement of iron oxide nanoparticles encapsulated with poly(D,L-lactide-co-glycolide)," Coll. Surf. A 255, 19-25 (2005).

Such particles are typically prepared using an oil-water, double-emulsion system; spray drying methods; supercritical conditioning methods; and milling methods. For further information on the creation of particles 106, see Jung-Hwan Park, et al. "Polymer Particle-Based Micromolding to Fabricate Novel Microstructures," Biomed Microdevices, Vol. 9, pp. 223-234 (2007) which is incorporated by reference above. Also, see J. Benoit, H. Marchais, H. Rolland, and V. V. Velde, *Biodegradable microspheres: Advances in production technology*. in Microencapsulaton: Methods and Industrial Application, edited by S. Benita (Marcel Dekker, New York, 1996) pp. 35-72; and J. H. Park, M. G. Allen, and M. R. Prausnitz, "Polymer microneedles for controlled-release drug delivery," Pharm. Res. Vol. 23, pgs. 1008-1019, (2006), such articles being incorporated herein by reference.

In addition, the particles 106 may comprise other materials such as, for example, poly(methylmethacrylate), polyethylene, polypropylene, or other polymers; metals; ceramics; or polymer or polymer-coated particles, or other appropriate materials.

A wide range of drugs may be included or encapsulated in the microstructures and methods. As used herein, the term "drug" is used broadly to refer to any prophylactic, therapeutic, or diagnostic agent, or other substance that may be suitable for inclusion in or on a microstructure or other structure, including pharmaceutical excipients and substances for tattooing, cosmetics, and the like. A drug can be a substance having biological activity. A drug formulation may include various forms, such as liquids, liquid solutions, gels, solid particles (e.g., microparticles, nanoparticles), or combinations thereof.

A drug may comprise small molecules, large (i.e., macro-) molecules, or a combination thereof. In representative, non-limiting, embodiments, the drug can be selected from among amino acids, vaccines, antiviral agents, DNA/RNA, gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, and vitamins. A drug may be selected from suitable proteins, peptides and fragments thereof, which can be naturally occurring, synthesized or recombinantly produced.

A variety of other pharmaceutical agents known in the art may be formulated for administration via the microstructures such as microneedles or other structures as described herein. Examples include beta-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors.

The particles 106 may comprise microparticles when they are used to fill a micromold and are thus appropriately sized to fit in the cavities 103. Also, the particles 106 may comprise different sizes and shapes.

Figure 1C:
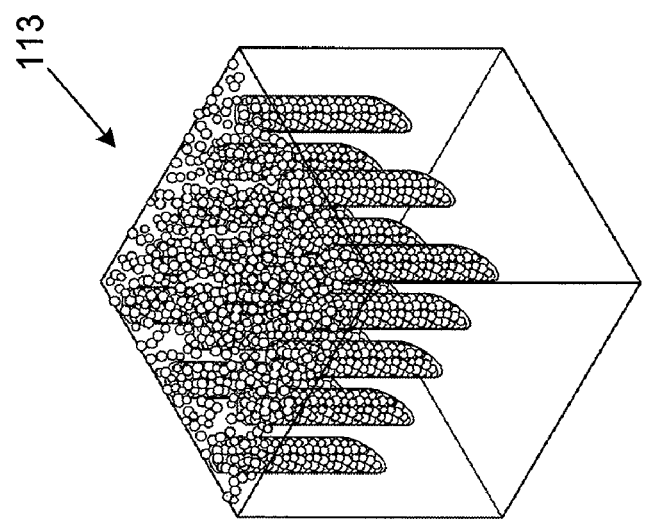

Referring once again to FIGS. 1A through 1F, next a method is described for creating a microstructure according to an embodiment of the invention. First, as depicted in FIG. 1A, the micromold 100 is covered with particles 106. As illustrated in FIG. 1B, a male master structure 109 is used to then push the particles 106 into the cavities 103 of the micromold 100. These steps are repeated until the cavities 103 are substantially full as depicted in FIG. 1C. In this manner, particles 106 are placed in the cavities 103 of the micromold 100. Alternatively, the particles 106 may be placed in the micromold 100 in some other manner. Also as shown, in some embodiments, a particle cake 113 is left on the exit side of the micromold 100.

Next, as depicted in FIG. 1D, a base substrate such as a PDMS sheet 116 (or sheet of other appropriate material) is placed onto the particle cake 113. Alternatively, the particle cake on the exit side of the micromold 100 may serve as a base substrate without the sheet 116. As an additional alternative, any appropriate structure may be used as the base substrate provided that can adhere to the structures formed in the cavities 103. Thus, as contemplated herein, the concept of a base substrate refers to any structure to which the structures created in the cavities of a mold (or micromold) can adhere as can be appreciated. Thereafter, in FIG. 1E, energy or a chemical treatment is applied to the micromold 100 in order to form a microstructure 119 in the micromold 100.

In one embodiment, the energy that is applied to the particles 106 is ultrasonic energy that causes adjacent ones of the particles 106 to be attached to each other. As depicted in FIG. 1D, a sonically reflective structure 121 may be placed under the micromold 100 opposite the exit side of the mold during the application of the ultrasonic energy to reflect sound waves back into the mold. The ultrasonic energy may be applied to the micromold 100, for example, by applying an ultrasonic horn 123 to the micromold 100 or to the PDMS sheet 116 as illustrated in FIG. 1E. Alternatively, ultrasonic energy may be applied using other well-known techniques such as, for example, immersion in an ultrasonically-excited water bath.

The application of ultrasonic energy to the micromold 100, whether it is directly to the micromold 100 or through the PDMS sheet 116, causes the local welding of adjacent particles 106 to each other. Local welding of adjacent particles 106 refers to the fact that the immediate surfaces of the particles 106 where particles 106 are in contact are altered so as to be attached to each other. For example, it is theorized that the movement of particles 106 next to each other due to the application of ultrasonic energy results in friction and heating of the particles 106 at the points of friction. Such heating results in local welding of the particles. It may be possible that the local welding results from other phenomena beyond heating.

Figure 1F:
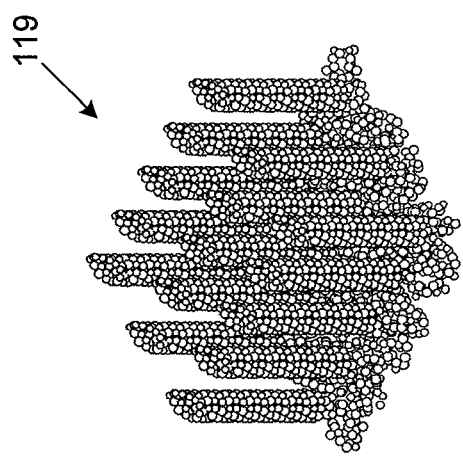
Figure 1E:
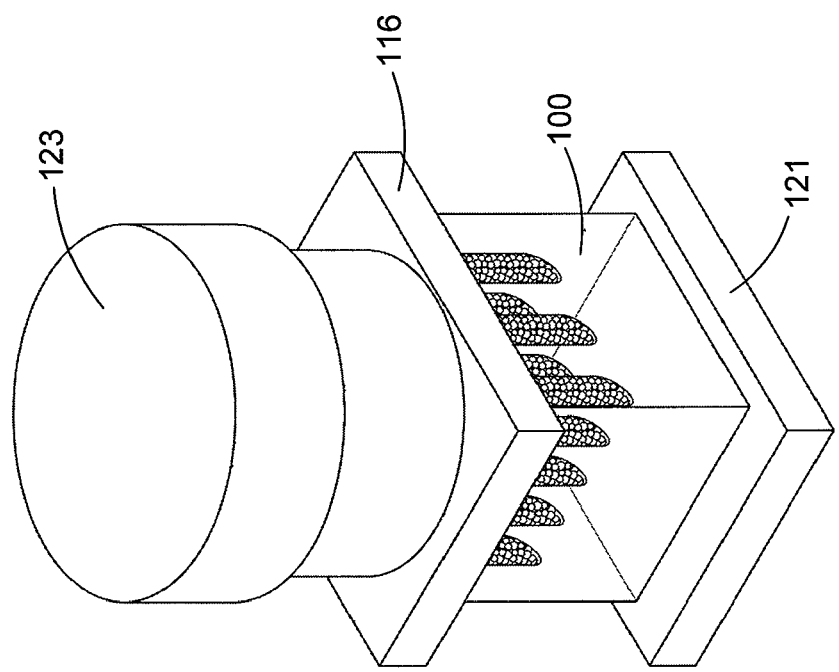

Once the ultrasonic energy has been added such that the desired local welding of the particles 106 has been accomplished, then the resulting microstructure 119 as depicted in FIG. 1F may be extracted from the micromold 100.

It should also be noted that it is possible that a mold other than a micromold 100 may be employed. Although there is no hard and fast rule as to when a mold is a micromold as opposed to a larger mold that is not classifiable as "micro," generally it can be asserted that molds that are "micromolds" are those that can be used to create structures having some physical dimension or feature that is less than or equal to 1 millimeter in size. It may be the case, for example, that a micromold 100 may be employed to create microstructures that are generally less than 1 millimeter in size, and yet are attached to a substrate that is much larger than 1 millimeter.

As depicted in FIGS. 1A-F and 2A-F, the structures shown therein comprise, for example, microstructures that are actually microneedles that may be inserted into biological tissue. Although microneedles are shown, it is understood that any other type of microstructure may be created using the principles described herein, where the microneedles are shown merely as an example. Also, it is understood that structures other than microstructures may be created using the principles discussed herein. Such structures may comprise, for example, stents, microfluidic networks, and neural interfaces.

The application of ultrasonic energy to the particles 106 in the micromold 100 or other mold provides various advantages. Among these advantages is the fact that the resulting microstructure 119 or other structure is porous in nature given that the particles 106 are not fully melted, thereby allowing substances to flow into and out of, or through the resulting microstructure 119 or other structure.

Thus, the microstructure 119 or other structure may be constructed so as to be porous in nature for specific application where such porosity is desired. For example, where in one application, a mold may be created for a stent that is used to expand arterial walls, etc. The porous nature of a structure created using ultrasonic energy as described above may be useful to allow tissue to grow and enmesh the stent or other device. The degree of porosity of the resulting structure may be determined in part based upon the size(s) of the particles 106 placed in the micromold 100 or other mold.

In addition, the local welding of particles 106 by the application of ultrasonic energy facilitates the creation of the microstructure 119 or other structure without unduly raising the temperature of an interior portion of the particles 106 themselves. To this end, local welding can be achieved without raising the temperature of the interior portion of the particles above a predefined threshold. Thus, the temperature in the interior portion of the particles 106 can be maintained at less than the predefined threshold during the local welding. This is advantageous where the particle 106 is composed of a substance that degrades at temperatures above the predefined threshold.

For example, the particles 106 may be made out of various biodegradable materials and may include various drugs or other substances that would be degraded or damaged if exposed to excessive heat. The local welding of particles 106 accomplished by way of ultrasonic welding prevents unwanted heating of the interior of the particles 106, thereby preventing unwanted degradation of substances such as drugs or other compounds that are to be released when the structure is inserted into a patient, etc. It is possible that heating that might occur at the sites of the local welds between particles 106 that might do damage to substances such as drugs and or other substances encapsulated in the particles 106. However, since the local welding is, in fact, localized to the sites where particles 106 are attached, the majority of the substances encapsulated in the particles 106 are left intact.

Alternatively, energy may be applied to the particles 106 by applying heat to the micromold 100 by placing the micromold 100 in an oven or via some other approach. Where the micromold 100 or other type of mold is placed in an oven, the resulting heat transferred to the particles causes the particles to melt either partially or completely. To the extent that particles 106 are mostly or completely melted, the microstructure 119 or other structure resulting therefrom may conform more completely to the shape of the mold. Such structures may have little or no porosity as can be appreciated. However, the structures maybe porous if the heat is applied in a short interval such as is the case with a partial melting of the particles 106.

In addition, it may be possible to apply energy to a mold in some other manner, such as exposure of a mold to an open flame, by use of induction or resistive (ohmic) heating, by mechanical vibration, or other approaches.

In addition, one or more chemicals can be applied to a micromold 100 to attach particles 106 within the micromold 100 to each other. Stated another way, the micromold 100 may undergo a chemical treatment. The resulting structure can have porosity or can have little or no porosity. In one embodiment, a chemical can be a solvent that dissolves one or more of the materials comprising the particles 106. This chemical can be provided as a liquid or as a vapor. A brief exposure of the micromold 100 to the chemical can dissolve or partially dissolve the outer portion of one or more particles 106, but have insufficient time to penetrate into the interior of the one or more particles 106. This would achieve a local welding of the particles 106 to each other. In one embodiment, this method could protect drugs encapsulated within particles 106 from exposure to the solvent, and thereby prevent solvent-based damage to the drug.

The brief exposure to the chemical could be achieved by adding liquid chemical into the micromold 100 and then removing the chemical by pouring it out, or by vaporizing it by increasing the temperature, lowering the pressure or other methods. The brief exposure to the chemical could also be achieved by adding a chemical vapor to the micromold 100 and then removing the chemical vapor by aerating the micromold 100, evacuating the micromold 100 or otherwise displacing the chemical vapor with another gas or vapor. A longer exposure to a chemical could similarly be achieved by leaving the chemical in the micromold 100 for a longer period of time.

Local welding of particles 106 to each other within the micromold 100 could also be achieved by altering the chemical environment in other ways. For example, the pH, ionic composition, ionic strength, viscosity, thermal conductivity, electrical conductivity, and other properties of the environment in the micromold 100 could be altered. In one embodiment, the surface properties of particles 106 could be such that they do not adhere to each other at a first pH, but do adhere to each other at a second pH, perhaps due to changes in the charge state of molecules located on the particle surface. In this way, particles 106 could be placed within a micromold 100 at the first pH and then adhered to each other within the micromold 100 by switching to the second pH.

Attachment of particles 106 to each other could also be achieved by stimulating a chemical reaction within the micromold 100. The chemical reaction could be stimulated actively by applying energy to the micromold 100, by altering the chemical environment in the micromold 100 or other methods. The chemical reaction could occur spontaneously upon placement of the particles 106 within the micromold 100, possibly after a time delay. In one embodiment, molecules on the surfaces of the particles 106 react with each other to form chemical bonds that attach the particles 106. In one embodiment, the reaction could be a polymerization reaction or a cross-linking reaction and could involving stimulation using ultraviolet light.

Figure 2A:
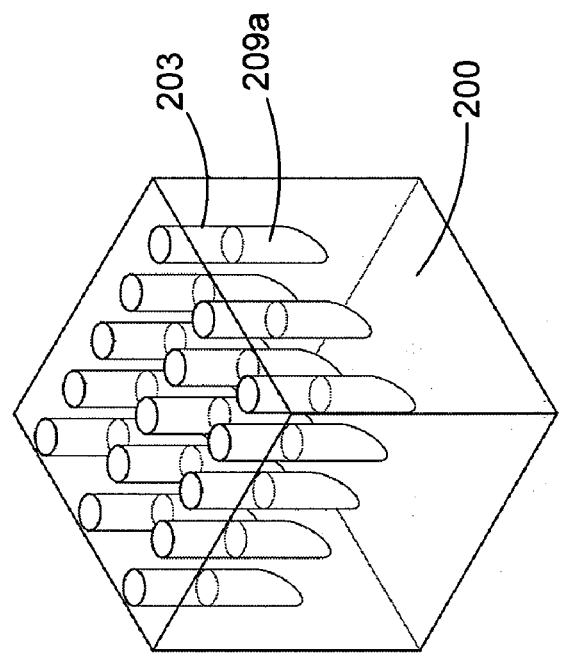
FIGS. 2A through 2F are drawings that illustrate the creation of further structures according to various embodiments of the present invention.

With reference then to FIGS. 2A though 2F, shown are steps of a method for creating a microstructure according to an embodiment of the invention. As shown in FIG. 2A, particles 206a are filled into the cavities 203 of a micromold or other mold (hereafter mold 200) in a manner similar to that described with reference to FIG. 1A. The particles 206a may be the same as the particles 106 described above. Note that the cavities 203 of the mold 200 may be fully or partially filled with particles 206a. In order to ensure that no particle cake is left on the top of the mold 200, adhesive tape may be pressed up against the top of the mold 200 to remove excess particles 200 from the mold 200.

Next, energy or a chemical treatment as described above is applied to the mold 200 to transform the particles 206a into structures 209a that conform with the cavities 203 of the mold. To apply energy to the mold 200, for example, the mold 200 may be placed in an oven and heated so that the particles 206a in the cavities 203 are at least partially melted and conform with the cavities 203 of the mold 200. Alternatively, ultrasonic energy may be applied to the mold 200 in a manner described above with respect to FIG. 1E. Where the particles 206a are substantially melted due to the application of energy in the form of heat, the resulting structures 209a formed in the cavities 203 are non-porous. Alternatively, where ultrasonic energy is applied, the structures 209a may be porous in nature.

Figure 2B:
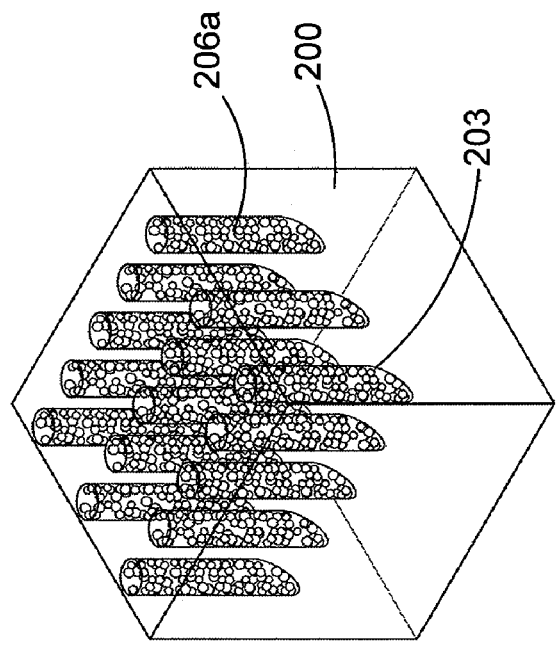

Also, where the particles 206a are substantially melted, the cavities 203 may ultimately be partially filled as the volume of the cavities 203 filled by the melted particles 206a is less than the volume filled by the particles 206a themselves due to the fact that voids between particles 206a are at least partially or entirely eliminated. As depicted in FIG. 2B, the particles 206a have been exposed to the needed amount of energy or the proper type of chemical treatment in order to melt or otherwise adhere the particles 206a together into nonporous structures 209a in the cavities 203. Note that the cavities 203 are thus partially filled.

Figure 2D:
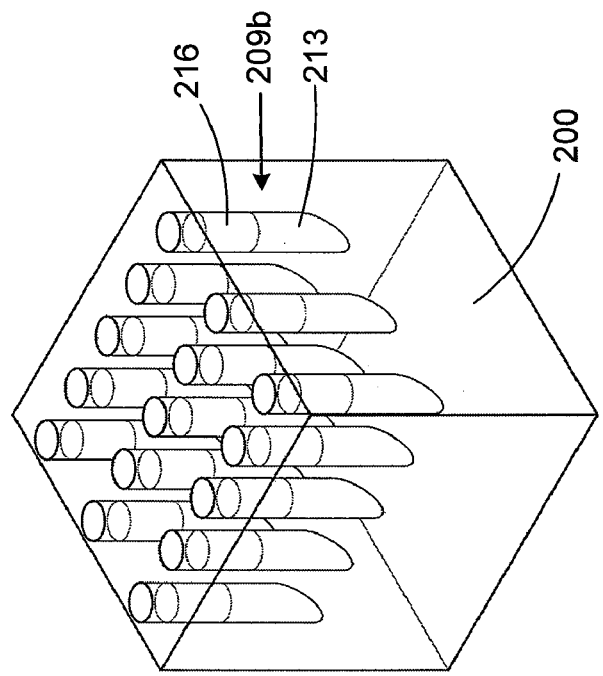
Figure 2C:
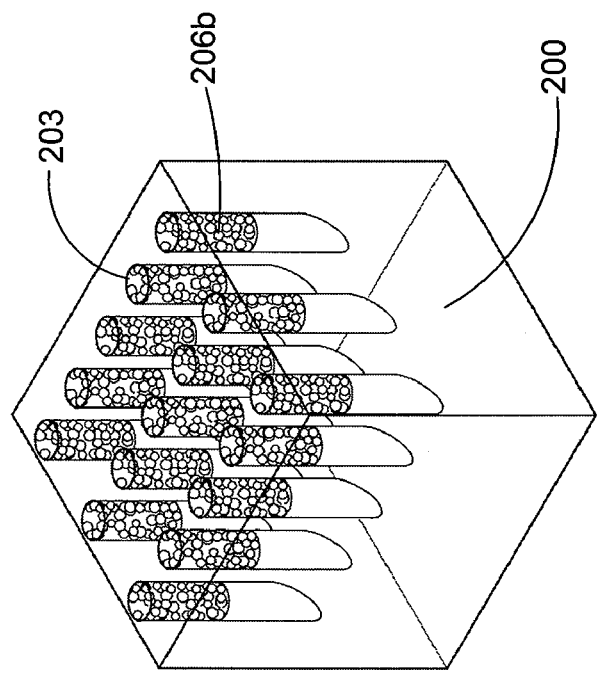
Figure 2F:
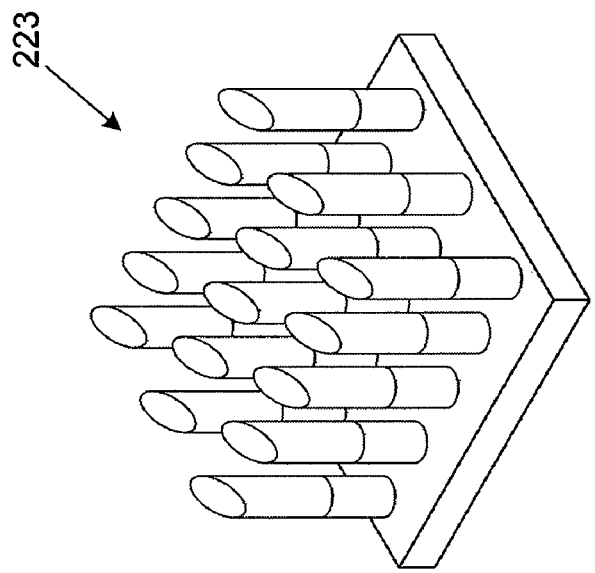

Next, as depicted in FIG. 2C, a second group of particles 206b is placed in the free volume of the cavities 203 after the particles 206a have been reduced by the application of energy. According to one embodiment, the particles 206b have a lower melting point than the particles 206a so that energy may be applied to melt the particles 206b without melting the structures 209a resulting from the reduction of the particles 206a. Alternatively, the particles 206b may react to a different chemical treatment from that which was applied to the particles 206a. As depicted in FIG. 2D, structures 209b are created that include a first layer 213 from the material of the particles 206a and a second layer 216 from the material of the particles 206b. The lower melting point of the particles 206b means that the second layer 216 can be added by melting the particles 206b without melting the first layer 213. Alternatively, the susceptibility of the particles 206b to a different chemical treatment than the particles 206a forming the first layer 213 means that the particles 206b can be chemically treated without affecting the first layer 213.

Alternatively, were ultrasonic energy is applied, there may not be much reduction due to the filling of voids between particles 206a or 206b, where a porous structure results.

According to one embodiment, several layers 213, 216 may be created in a given cavity 203 of a mold 200. The volume of each of the layers 213, 216 can be determined based upon the volume of particles 206 of a given size added that can be reduced to a single volume due to the addition of energy to the mold 200. Although only 2 layers are shown, it is understood that many different layers can be created in this manner.

In another embodiment, the particles 206a and 206b may be mixed before being placed in the cavities 203 of the mold. Thereafter, energy or chemical treatment may be applied to cause either local welding or melting of the particles as discussed above.

The particles 206a and 206b may be comprised of different compositions. For example, such different compositions may comprise the inclusion or encapsulation of different substances in the different particles 206a and 206b. Such different substances may comprise, for example, different drugs in the case where the structures created are to be inserted into biological tissue for the timed release of drugs, etc.

Figure 2E:
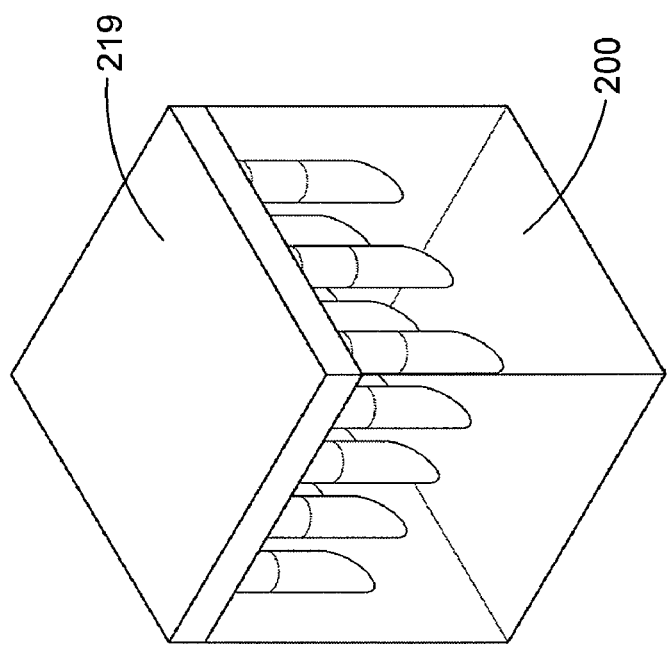

Next, in FIG. 2E, a base substrate 219 is formed by applying energy or chemical treatment to a particle cake placed at the exit side of the mold 200. Alternatively, the base substrate 219 may comprise a sheet of material placed over the mold 200 and attaching the sheet of material to the structures 209b via the application of a chemical treatment or by the application of energy by way of heating, ultrasonic welding, or via some other energy source. As an additional alternative, any structure may be used as a base substrate provided that you can adhere the structures 209b to such structure. After the application of energy or chemical treatment to the mold 200 for the last time, the resulting structure 223 is extracted from the mold 200.

By virtue of the fact that the structure 223 is formed from particles 206 of multiple different compositions, the composition of the structure 223 is described herein as non-homogenous. As contemplated herein, the term non-homogenous refers to structures that differ in composition such as combinations of different polymers or combinations of polymers with different materials, or combinations of polymers with portions without material such as voids. Depending upon the form of energy or the chemical treatment applied to the mold 200, the resulting structure 223 may also be porous or non-porous as described above. Also, the structure 223 may be a microstructure where the mold 200 is a micromold.

With reference to FIGS. 3A through 3D, shown are various steps of a method of creating a composite structure 300 according to an embodiment of the present invention. The composite structure 300 may comprise, for example, a reentrant structure. Also, the composite structure 300 may be, for example, a composite microstructure or other structure. A composite structure 300 comprises a single new structure that is created from two structures that are attached or otherwise put together. A reentrant structure is "reentrant" in the sense that it involves inserting or "reentering" a first structure into a mold in order such that a second structure created in the mold during the reentry by the first structure adheres to and becomes part of a common composite structure 300.

Figure 3B:
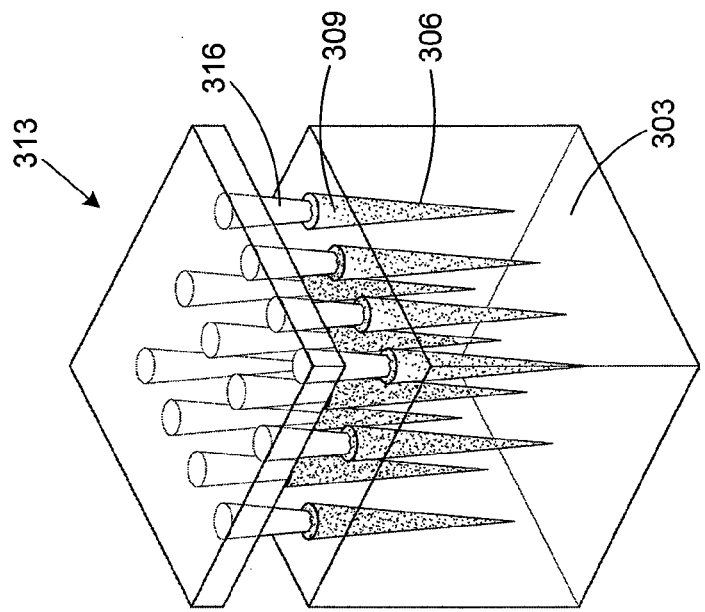
FIGS. 3A through 3D are drawings that illustrate the creation of composite structures according to an embodiment of the present invention.
Figure 3A:
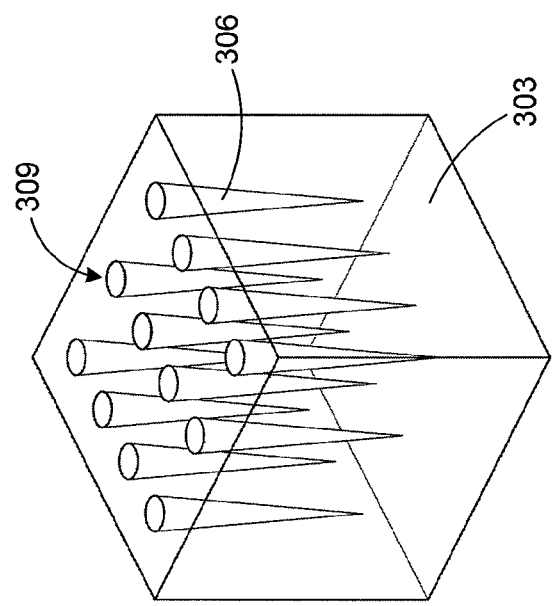

Turning to FIG. 3A, shown is a mold 303 with cavities 306 that have been filled with particles 309. The cavities 306 are not filled entirely with the particles 309 in order to allow room for the insertion of a first structure as will be described.

As depicted in FIG. 3B, a first structure 313 is positioned over the mold 303 and at least one portion of the first structure 313 is inserted into a cavity 306 of the mold 303 with the particles 309. As shown, the first structure 313 includes a number of needle-like structures 316 that extend from a base substrate. Alternatively, the first structure 313 may comprise a single needle-like structure 316.

Figure 3D:
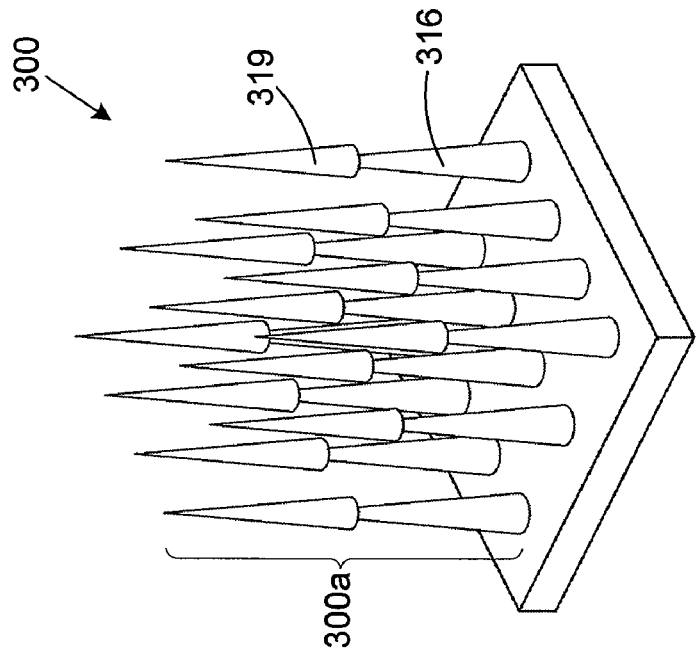
Figure 3C:
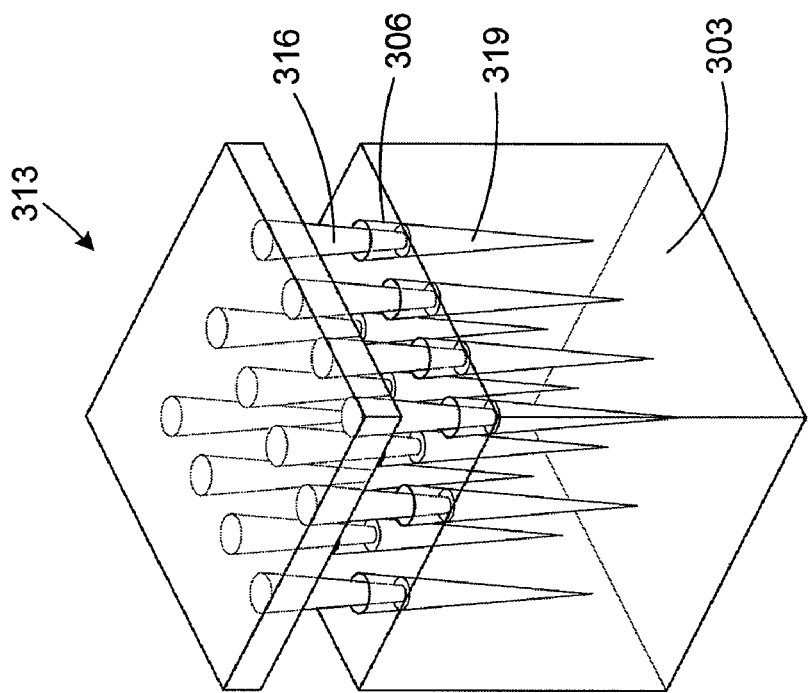

Once the first structure 313 is partially inserted or "reentered," for example, into the cavities 306, then energy or a chemical treatment is applied to the particles 309 in the cavities 306 of the mold 303. The energy applied may be in the form of heat, for example, where the mold 303 is placed in an oven. As depicted in FIG. 3C, according to one embodiment, the particles 309 in each of the cavities 306 are at least partially melted into a plurality of second structures 319, each second structure 319 adhering to a respective needle-like structure 316 of the first structure 131. In yet another embodiment, a chemical treatment may be applied that results in the creation of the second structures 319 and the adherence of second structures 319 to the first structure 131 in a similar manner.

As depicted in FIG. 3C, the volume of the particles 309 in the cavities 306 is reduced due to the melting or chemical alteration of the particles 309 and the filling of voids between the particles 309. The first and second structures 313/316 form the composite structure 300. The composite structure 300 is removed from the mold 303 as shown in FIG. 3D. Alternatively, the structure 300 may be considered to include multiple "arrowhead-like" composite structures 300a that are mounted on a base substrate.

According to one embodiment, the same mold 303 is advantageously used to create the first structure 313 and the second structures 319. In order to create the first structure 313, the particles 309 are placed in the cavities 306 of the mold 303 and the first structure is created as set forth above with a base substrate such as a particle cake, a sheet of material or other structure as described above with reference to FIGS. 1A through 2F. Alternatively, two different molds 303 may be employed to create the composite structure(s) 300/300a. Specifically, where two different molds are employed, a portion of the first structure would reenter a second mold so that second structures that differ can adhere thereto to form the ultimate composite structure.

According to one embodiment, a melting point of the first structure 313 is higher than the melting point of the particles 309 from which the second structures 319 are formed. Thus, assuming that the assembly represented by the structure 313 reentered into the mold 303 as depicted in FIG. 3C, is placed in an oven set at a temperature that is between the melting points of the first structure 313 and the particles 309, the first structure 313 will not melt while the particles 309 melt to form the second structure(s) 319. Alternatively, application of ultrasonic energy to the mold 303 may not cause much to change in the first structure 313 while causing the particles 309 to adhere to each other and to the first structure 313.

Also, the first structure 313 may be subject to a first chemical treatment and the particles 309 may be subject to a second chemical treatment that differs from the first chemical treatment. As such, the application of the second chemical treatment to the particles 309 will not cause the first structure 313 to be adversely affected. In still another embodiment, the same chemical treatment may be applied to both the first structure 313 and the particles 309 with such a time duration or concentration, or in some other manner, etc., that the particles 309 form a second structure adhered to the first structure 313 without unacceptably affecting the first structure 313.

In addition, the first structure 313, the needle-like structures 316, the second structures 319, and the composite structures 300/300a may all be microstructures as described above.

In one embodiment, the approach described with reference to FIGS. 3A through 3D advantageously provide a way to create a structure that might normally require a mold to be taken apart in pieces to facilitate extraction. This approach is especially useful on a micro-scale in which molds comprising two or more pieces to create a mold cavity do not exist.

Figure 4:
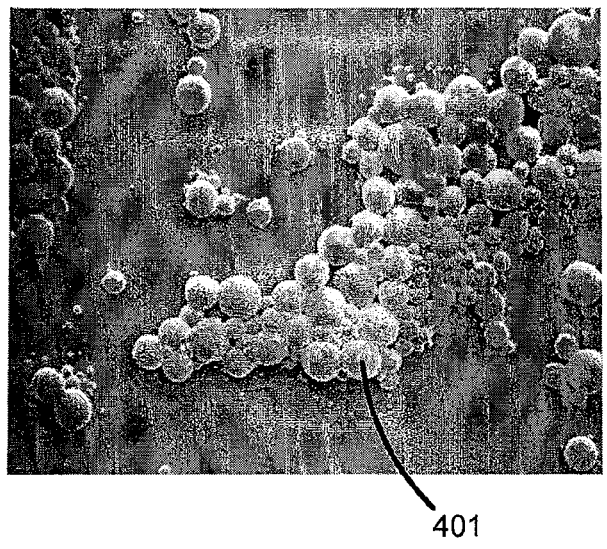
FIG. 4 is a picture of particles employed to create the structures described in FIGS. 1A through 3D according to an embodiment of the present invention.

Referring next to FIG. 4, shown is an image of particles 401 that may be used as the particles 106, 206a, 206b, 306 according to the various embodiments of the present invention. The particles 401 were created using a spray-drying technique, although other standard powder formation techniques could be used. The particles 401 generally are measured to be approximately 25 µm or less.

Figure 5:
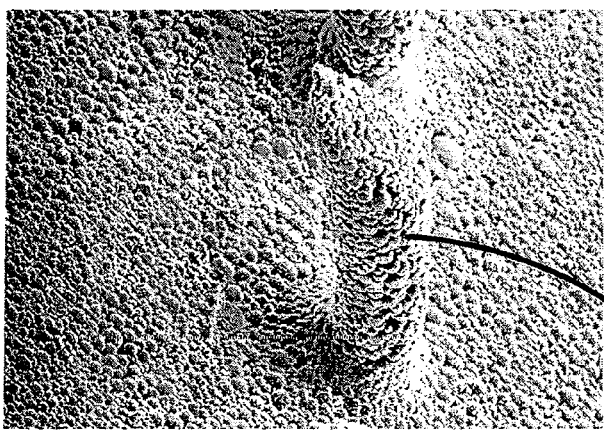
FIG. 5 is a picture of an example of a structure created as illustrated in FIGS. 1A through 1F according to an embodiment of the present invention.
Figure 6:
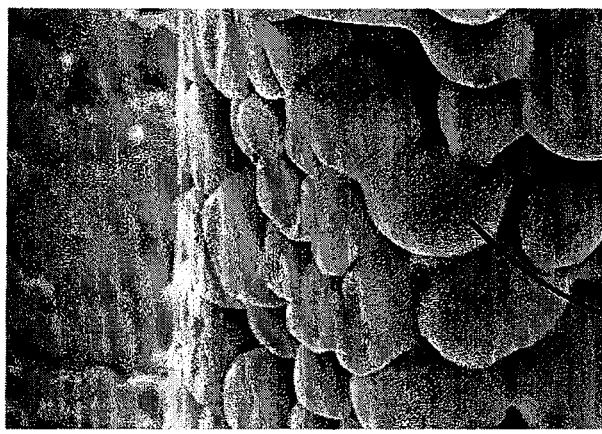
FIG. 6 is a picture that shows a portion of the structure of FIG. 5 according to an embodiment of the present invention.

With reference to FIG. 5, shown is an image of an actual microstructure 501 that was formed by the application of ultrasonic energy as described above according to various embodiments of the present invention. The image of FIG. 6 shows a closeup view of a portion of the microstructure 501 in which it is seen that adjacent particles are locally welded together by the application of ultrasonic energy according to various embodiments of the present invention.

It should be emphasized that the above-described embodiments of the present invention, are merely possible examples of implementations set forth for a clear understanding of the various embodiments of the invention. Many variations and modifications may be made to the above-described embodiment(s) of the invention without departing substantially from the spirit and principles of the invention. All such modifications and variations are intended to be included herein within the scope of this disclosure and the various embodiments of the present invention and protected by the following claims.

The invention claimed is:

1. A method, comprising the steps of:
   placing a plurality of first polymeric particles into a micromold;
   placing a plurality of second polymeric particles into the micromold, the second polymeric particles coming into contact with the first polymeric particles;
   applying ultrasonic energy to the first and second polymeric particles in the micromold, thereby forming a first microstructure and a second microstructure, respectively in the micromold out of the particles, wherein the energy causes the first microstructure to adhere to the second microstructure, thereby forming a composite microstructure; and
   removing the composite microstructure from the micromold.

2. The method of claim 1, further comprising the step of placing a base substrate at an exit side of the micromold, where the ultrasonic energy is applied to the base substrate.

3. The method of claim 1, wherein a physical dimension of the first microstructure is less than 1 millimeter.

4. The method of claim 1, further comprising the step of placing a sonically reflective structure under the micromold opposite the exit side of the micromold during the application of the ultrasonic energy to the micromold.

5. The method of claim 1, wherein a drug is included in at least one of the first and second polymeric particles.

6. The method of claim 1, wherein a melting point of the second polymeric particles are higher than the melting point of the first polymeric particles.

* * * * *